United States Patent [19]
Ziffer et al.

[11] Patent Number: 5,171,676
[45] Date of Patent: Dec. 15, 1992

[54] METHOD OF INTRODUCING HYDROXYL GROUPS INTO ARTEMISININ AND ITS DERIVATIVES

[75] Inventors: Herman Ziffer, Kensington; Yulin Hu, Bethesda, all of Md.

[73] Assignee: The United States of America as represented by the Secretary of the Department of Health and Human Services, Washington, D.C.

[21] Appl. No.: 785,993

[22] Filed: Oct. 31, 1991

[51] Int. Cl.$^5$ .................. C12P 17/08; C12P 17/06; C12R 1/645
[52] U.S. Cl. ................... 435/124; 435/125; 435/254; 435/911; 514/450; 549/348
[58] Field of Search .............. 549/348; 514/450; 435/124, 125, 911, 254, 25

[56] References Cited
PUBLICATIONS

Lee et al. (1989) The Journal of Natural Products 52(2): 337–341.
Baker et al., (1988) Biomedical and Environmental Mass Spectrometry 18:337–351.
Lee et al. (1990) Pharmaceutical Research 7(2):199–203.
Chem Abst 14–127(1) Hufford et al. "Pharm Res (Phreeb)" v7 (9), pp. 923–927 (1990).
Biotech Abst. 87–03099 Marakby et al. "Pharm Res" (1986) 3,5, Suppl. 215.
BioTech Abs 91–14058 Hu et al. ASCRAL "Abs Pap Am Chem Soc" 1991 (202) Pt I BioTech 170.
BioTech Abs 91–12895 Hu et al. JCCCAT "J. Chem. Soc. Chem. Comm" (1991) 17 pp. 1176–1177.

*Primary Examiner*—Herbert J. Lilling
*Attorney, Agent, or Firm*—Birch, Stewart, Kolasch and Birch

[57] ABSTRACT

The fungus Beauveria sulfurescens has been employed to introduce hydroxyl groups into artemisinin and derivatives of artemisinin, an antimalarial. Hydroxylated derivatives of artemisinin and derivatives of artemisinin produced thereby possess antimalarial activity, and can serve as intermediates in the synthesis of further derivatives useful in treating malaria.

13 Claims, 2 Drawing Sheets

METHOD OF INTRODUCING HYDROXYL GROUPS INTO ARTEMISININ AND ITS DERIVATIVES

BACKGROUND OF THE INVENTION

1. Field of the Invention

The present invention relates to the production of derivatives of the antimalarial artemisinin. More specifically, the present invention relates to the production of artemisinin derivatives via microbial hydroxylation under conditions that preserve the peroxide bridge moiety necessary for antimalarial activity. Hydroxylated derivatives of artemisinin can be employed to produce useful alternatives to artemisinin itself.

2. Description of Related Art

Formidable problems encountered in developing a malaria vaccine (1) and the ability of *Plasmodium falciparum* to become resistant to new drugs (2) have stimulated interest in using combinations of drugs for treating this disease, which claims more than a million lives a year (3).

The occurrence of a number of drug resistant strains of malaria makes it unlikely that a single drug will be effective in treating both resistant and non-resistant parasites. Recent reports by Van Dyke et al. (2) describing the use of compounds, e.g., verapamil, tetrandrine, etc., to reverse the chloroquine-resistance in *Falciparum malaria* promise to rejuvenate efforts to find new combinations of drugs to treat malaria. Van Dyke has also demonstrated that these compounds act in a synergistic manner to greatly reduce the quantities of drugs required for activity. Verapamil and tetrandrine apparently act by interfering with a mechanism in malarial parasites that rapidly expels drugs and foreign compounds from the cell's interior. Similar mechanisms apparently provide multidrug resistance in cancer cells (13). As pharmacologists and others develop a better understanding of these mechanisms, they will be able to formulate strategies to circumvent these mechanisms and treat these diseases with drugs. Such short term solutions will permit others to complete the research efforts required to formulate ways of treating malaria and similar diseases with vaccines.

The finding by Van Dyke showing that there are mechanisms (pumps) in malaria parasites to remove foreign substances (drugs) before they act, and the existence of molecules capable of stopping this "pumping" action, should stimulate efforts to identify combinations of fast and slow acting drugs that can effectively be used to treat patients with malaria.

One drug of current interest for which *P. falciparum* has not developed resistance is artemisinin, (I), (qinghaosu) (4). First isolated by Chinese investigators (5) from a traditional medicinal herb, *Artemisia annua* L., it has also been isolated from Artemisia species in the U.S. (6). Qinghaosu has been shown to act rapidly and to be relatively non-toxic.

A report by Chinese investigators that the active component of an herb used to treat malaria is a sesquiterpene, artemisinin, aroused enormous interest in employing derivatives of this rapidly acting compound, which is structurally different from quinine and other antimalarials (2). In order to prepare derivatives with enhanced solubilities in water and in lipids, it was first necessary to reduce the lactone to a ketal that possess a hydroxyl group. Carbonates, esters, and ethers of dihydroartemisinin were prepared and tested. Results of those tests demonstrated that the peroxide bridge was absolutely essential for activity (5).

Investigators from the "Coordinating Clinical Study Group on Qinghaosu" prepared the first derivatives of dihydroartemisinin in China and employed them to treat 1511 cases of *vivax* malaria and 588 cases of *falciparum* malaria between 1973 and 1978 (12). The compounds uniformly yielded clinical cures. The most potent derivatives found by these investigators were carbonates. The second most active group of dihydroartemisinin derivatives was esters, followed by ethers. A major shortcoming of this work was the high recrudescence rate. In order to overcome this problem, new derivatives of dihydroartemisinin were sought.

Lee et al (10a) and (10b) have shown that microbial oxidation of artemisinin and arteether by a number of fungi yields products in which the peroxide bridge is replaced by an oxide. Such products are neither active against malaria, nor can they be converted into antimalarial drugs.

SUMMARY OF THE INVENTION

The presence of a single hydroxyl group in artemisinin limits the number and kinds of derivatives thereof that can be prepared. The introduction of a second hydroxyl group greatly increases the number of possible structural modifications, and permits, for the first time, variation of different parts of the molecule. As noted supra, the most potent derivatives found by the Chinese investigators from the "Coordinating Clinical Study Group on Qinghaosu" (12) were carbonates. The second most active group of dihydroartemisinin derivatives was esters. The presence of a second hydroxyl group allows investigation of the effects due to the presence of, for example, a second carbonate or a second ester.

As the peroxide bridge is easily destroyed, the present inventors elected to determine if a microbial method could be employed to introduce a hydroxyl group on one of the unactivated methyl or methylene groups of the molecule. The addition of a second functional group greatly increases the number of derivatives that can be prepared, and enables study of the effect of altering different regions of the molecule on its biological activity.

As a first step toward the preparation of such novel derivatives, the present inventors have employed a fungus, *Beauveria sulfurescens*, to introduce hydroxyl groups into these molecules onto unactivated methyl or methylene groups therein. Initial studies employing the N-phenylurethane of dihydroartemisinin demonstrated that the hydroxyl group introduced by the enzymes of B. sulfurescens was on one of the methyl groups. This led to the discovery that B. sulfurescens can insert hydroxyl groups at C-7 and C-14 in artemisinin derivatives while retaining the peroxide bridge necessary for antimalarial activity.

Preliminary in vitro tests indicate that the resultant compounds and subsequent derivatives thereof are active against resistant and non-resistant strains of *P. falciparum*. Thus, microbial hydroxylation now makes possible the preparation of a wide variety of new compounds with anti-malarial activity that were not previously accessible.

Accordingly, it is an object of the present invention to provide a method for hydroxylating a substrate selected from the group consisting of artemisinin, dihydroartemisinin, and a derivative of dihydroartemisinin, comprising incubating said substrate in the presence of a microorganism capable of introducing a hydroxyl group therein, while preserving the peroxide bridge therein, thereby producing a hydroxylated derivative of said substrate.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWING

The above and other objects, features, and advantages of the present invention will be better understood from the following detailed descriptions taken in conjunction with the accompanying drawing, all of which are given by way of illustration only, and are not limitative of the present invention, in which.

DETAILED DESCRIPTION OF THE INVENTION

Figure 1A:
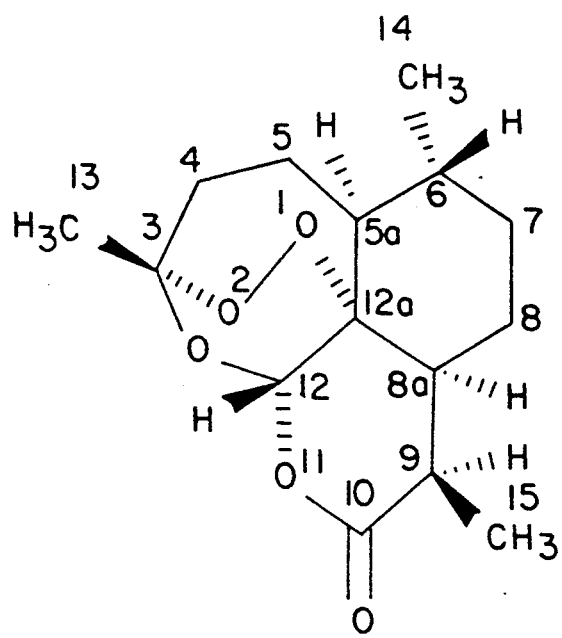
FIG. 1 depicts the structure of artemisinin (I) and various derivatives thereof discussed herein.
Figure 1B:
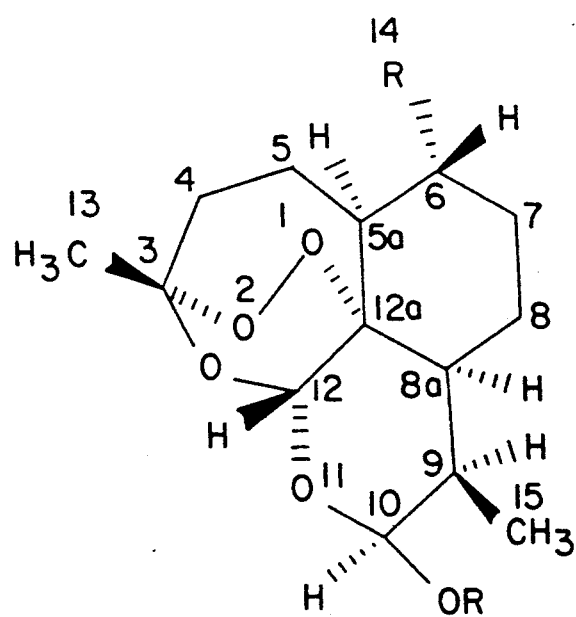
Figure 1C:
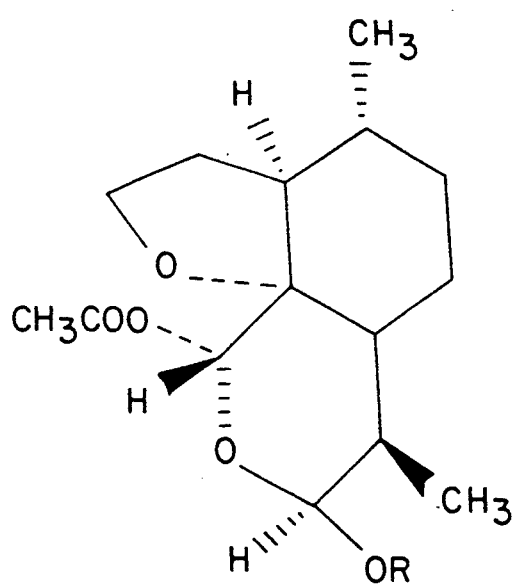

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

ARTEMISININ

Artemisinin is available in large quantities from natural sources such as *Artemisia annua L.* The expertise required to convert it into an active compound is well known in the art.

PREPARATION OF THE STARTING MATERIAL

Earlier studies with *B. sulfurescens* disclosed that very poor hydroxylation substrates could be converted into acceptable ones by introducing an amide group that appears to enhance bonding between substrate and the hydroxylating enzyme complex. The substrate chosen for the work described herein is a derivative of dihydroartemisinin, (III), prepared by the procedure of Brossi et al. (8), which yielded a hydroxylated derivative, (IV), while retaining the peroxide grouping required for biological activity. Its structure was established by mass spectroscopic, $^1$H, and $^{13}$C nmr studies.

MICROBIAL PRODUCTION OF DIHYDROXYDIHYDROARTEMISININ

Earlier studies by Hufford et al. (10) on the action of a number of fungi on (I) and (V) identified several transformation products in which the peroxide bridge had been destroyed. The present selection of Beauveria sulfurescens was based on reports that this fungus accepts a variety of substrates (11), and studies conducted by the present inventors with p-alkyl-N-acetylaniline. Also useful in the present invention are mutants of *B. sulfurescens* capable of hydroxylating derivatives of artemisinin.

EXAMPLE 1

*Beauveria sulfurescens* was grown in three liter flasks each containing 250 ml of media prepared from 20 gm. dextrose and 10 gm. neopeptone per liter, for two days. The mycelia were then separated and resuspended in 200 ml of phosphate buffer (0.1M), pH 7.5, and (III) was added (300 mg in 2.4 ml dimethylformamide). After shaking for 3 days, the mycelia and buffer were extracted with ethyl acetate, and a UV-absorbing transformation product was isolated by flash chromatography on silica gel employing ethyl acetate-hexane (40:60) as eluent. Further purification by HPLC using the same solvent system yielded (IV) $\partial a[_D^{25°\ C.}\ -22.8°$ (c 0.1, MeOH) in 3.4% yield. Its mass spectrum ($^{252}$Cf plasma desorption) exhibited a peak at m/z 442 (Mol. ion+Na+), corresponding to addition of 16 mass units, consistent with the insertion of an oxygen atom. The $^1$H spectrum showed the presence of only two methyl groups with a new multiplet (2H) at δ 3.48. One of the methyl groups, the singlet at δ 1.4, corresponds to the C-13 methyl. The doublet at δ0.94 was assigned to the C-15 methyl by a multiple quantum filtered COSY spectrum, which showed that the multiplet at δ 2.6 (H-9) is coupled both to the doublet at δ 0.94 and to that at δ 5.78 (H-10). The methyl at C-6 had therefore been converted into a hydroxymethyl group. A DEPT experiment and heteronuclear correlation spectrum confirmed that the methylene carbon at δ 64.6 bears the protons at δ 3.48. The presence of the peroxide group, implied by the molecular weight, was deduced from a comparison of the $^{13}$C chemical shifts for the quaternary carbons (δ 104.5 and 80.2) at the terminus of the peroxide bridge, in (III) and (IV). The relevant chemical shifts (Table 1) were essentially identical, consistent with the continued presence of the group.

TABLE 1

| Summary of $^{13}$C chemical shift assignments | | | | | |
|---|---|---|---|---|---|
| Carbon | I δ | III δ | IV δ | VIa δ | VIb δ |
| 3 | 105.22 | 104.55 | 104.53 | 168.46 | 169.3 |
| 4 | 35.77 | 36.33 | 36.22 | 68.76 | 68.6 |
| 5 | 24.79 | 24.66 | 24.19 | 27.6 | 27.8 |
| 5a | 49.90 | 52.63 | 45.96$^a$ | 54.99 | 55.7 |
| 6 | 37.42 | 37.35 | 44.29$^a$ | 33.95 | 30.6 |
| 7 | 33.45 | 34.19 | 28.36 | 35.46 | 35.9 |
| 8 | 23.32 | 22.02 | 21.73 | 22.59 | 24.7 |
| 8a | 44.80 | 45.41 | 45.22 | 47.40 | 47.1 |
| 9 | 32.78 | 31.85 | 31.89 | 30.42 | 33.3 |
| 10 | 171.92 | 93.08 | 93.10 | 94.51 | 101.7 |
| 12 | 93.62 | 91.55 | 91.40 | 90.98 | 88.4 |
| 12a | 79.38 | 80.20 | 80.27 | 80.07 | 80.6 |
| 13 | 25.10 | 25.83 | 25.90 | 21.39 | 21.6 |
| 14 | 19.74 | 20.24 | 64.64 | 20.45 | 20.5 |
| 15 | 12.47 | 12.15 | 12.20 | 12.01 | 12.5 |
| 1' | | 137.70 | 137.51 | 137.44 | |
| 2',6' | | 118.88 | 118.84 | 118.94 | |
| 3',5' | | 128.91 | 129.03 | 129.02 | |
| 4' | | 123.47 | 123.71 | 123.75 | |
| C-O | | 152.05 | 151.89 | 151.60 | |

$^a$May be interchanged.

The data presented above confirm that B. sulfurescens can convert the N-phenylurethane of dihydroartemisinin into a derivative containing a hydroxyl group on the C-6 methyl group, as depicted below:

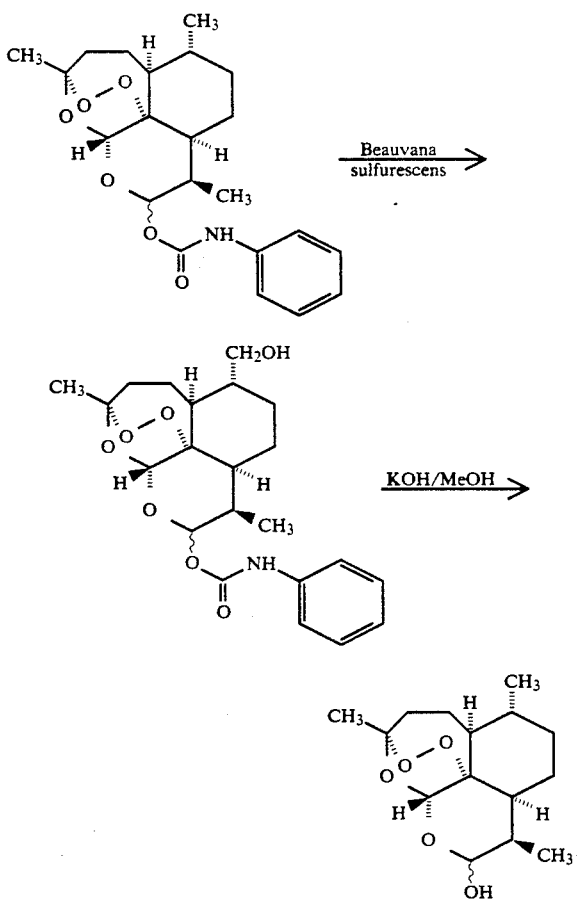

EXAMPLE 2

Since a significant amount of starting material was recovered using the above reaction conditions, a number of small-scale experiments were conducted in an effort to increase the yield in the biotransformation. It was found that if the mycelia obtained from 250 ml of media were resuspended in 100 ml of buffer and reacted with 20 mg of the substrate, the yield of the biotransformation increased to 15%.

EXAMPLE 3

In exploring the role the media played in stimulating the mycelia to produce high levels of the hydroxylating enzyme complex, B sulfurescens was also grown on corn steep liquors as described by Johnson (11). The mycelia were isolated, resuspended in phosphate buffer at pH 7.5, and (III) was added. After three days, the reaction mixture was worked up as described above to yield a different metabolite, (VIa), with a molecular weight isomeric with the starting material. Its structure was assigned by $^1$H and $^{13}$C nmr spectroscopy. Hufford et al. (10b) reported the formation of a similar metabolite, (VIb), from (V). The $^{13}$C chemical shifts of (I), (III), (IV), (VIa), and (VIb) and their assignments are given in Table 1, supra.

EXAMPLE 4

Beauveria sulfurescens (ATCC 7159) grown on Sabouraud Liquid Broth modified Antibiotic medium 13 (BBL, Cockeysville, Md.) solidified with 2% agar was inoculated into 250 ml of the same liquid medium in a 1 liter Erlenmeyer flask. The flask was shaken at 200 rpm at 27° for 72 hours. Aliquots of this culture were employed to inoculate twelve 1 liter Erlenmeyer flasks containing 250 ml of medium and approximately 100 μg of arteether. The flasks were shaken at 200 rpm at 27° C. for 72 hours. The mycelia were then collected by filtration, and resuspended in 200 ml of 0.2 M KH$_2$PO$_4$ buffer, pH 7.5. Arteether (40 mg in 0.4 ml of ethanol) was then added to each flask. The flasks were then shaken for three days; the mycelia were removed by filtration and the combined filtrates were extracted with ethyl acetate. The extracts were dried and concentrated. The residue was purified by flash chromatography on silica gel. The first metabolite eluted was 3α-hydroxyldesoxyarteether (27 mg), the second 7β-hydroxyarteether (72 mg), and the third 14-hydroxyarteether (110 mg).

The ability of the fungus B. sulfurescens to hydroxylate the C-14 methyl of artemisinin derivatives has enabled the present inventors to employ the reaction product obtained from arteether, the ethyl ether of dihydroartemisinin, in conjunction with conventional chemistry, to incorporate one or two deuterium (tritium) atoms on the C-14 methyl group of arteether. Since very little of a label at this position is removed during the drug's metabolism, labelled arteether may be useful in a variety of biological studies. Preliminary results on the antimalarial activity of (IV), below, support the conclusion of earlier structure-activity studies that the intact peroxide bridge is important for antimalarial activity.

The successful preparation of an intermediate, (IV), that can be employed to prepare radiochemically labelled samples of (I) or (II) in which the label is metabolically stable for studying the mode of action of these compounds represents a major advance. In addition, the intermediate can be employed to prepare new longer acting and more potent antimalarials.

EXAMPLE 5

Antimalarial activity of hydroxylated dihydroartemisinin derivatives.

The antimalarial activity of various hydroxylated artemisinin derivatives obtained via the present method was determined by Drs. S. Anderson and W.K. Milhous at the Division of Experimental Therapeutics, Walter Reed Army Institute of Research, Washington, D.C.

The malarial strains employed in this survey include D6, W2, and GA3. In Table 2, below, the -pharmacological data are reported as IC-50, indicating the concentration, in ng per ml, of compound required to inhibit growth of the parasite at the 50% level. The smaller the indicated value, the more active the compound against the malarial parasite. For comparative purposes, control experiments were conducted employing arteether and artemisinin, the most effective artemisinin derivatives known to date, as well as chloroquine.

TABLE 2

Antimalarial Activity of Dihydroartemisinin Derivatives Against Plasmodium falciparum In Vitro

| Compound | Malarial Strain | IC-50, ng/ml |
|---|---|---|
| 14-Hydroxy-N-phenylcarbamoyl dihydroartemisinin (IV) | D6 | 2.0 |
| 7β-Hydroxyarteether | D6 | 12.6 |
|  | W2 | 2.78 |
|  | GA3 | 8.83 |

TABLE 2-continued

Antimalarial Activity of Dihydroartemisinin Derivatives Against *Plasmodium falciparum* In Vitro

| Compound | Malarial Strain | IC-50, ng/ml |
|---|---|---|
| 14-Hydroxyarteether | D6 | 12.6 |
| | W2 | 2.77 |
| | GA3 | 8.18 |
| Artemisinin | D6 | 0.97 |
| | W2 | 0.79 |
| | GA3 | 1.58 |
| Arteether | D6 | 0.73 |
| | W2 | 0.28 |
| | GA3 | 0.498 |
| Chloroquine | D6 | 6.63 |
| | W2 | 41.38 |

As shown by the data in Table 2, 14-hydroxy-N-phenylcarbamoyl dihydroartemisinin (IV), 7β-hydroxyarteether, and 14-hydroxyarteether, products obtained via the microbial hydroxylation process described herein, exhibit antimalarial activity against the strains tested. This demonstrates the utility of compounds obtained via the present inventive method.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

LITERATURE CITED

1. Chemical and Engineering News, 399–403, 1990.
2. (a) Z. Ye, K. Van Dyke, and V. Castranova, Biochem. Biophys. Res. Commun. 165, 758 (1989) (b) Z. Ye and K. Van Dyke, ibid. 159, 242 (1989) (c) Z. Ye and K. Van Dyke, ibid. 155, 476 (1988)
3. "Tropical Diseases, Progress in International Research," 1987–1988, 43–54, WHO Special Programmed for Research and Training in Tropical Diseases, 1989.
4. D. L. Klayman, Science, 228, 1049 (1985).
5. Qinghaosu Antimalarial Coordinating Research Group, Chinese Medical Journal, 92, 811 (1979).
6. D. L. Klayman, A. J. Lin, N. Acton, J. P. Scovill, J. M. Hoch, W. K. Milhous, A. D. Theocharides and A. S. Dobek, J. of Natural. products, 47, 715 (1984).
7. (a) China Cooperative Research Group on Qinghaosu, J. of Traditional Chinese Medicine, 2 (1) 9-16 (1982) (b) A. Brossi, B. Venugopalan, L. D. Gerpe, J. J. C. Yeh, J. L. Flippen-Anderson, P. Buchs, X. D. Luo, W. Milhous, and W. Peters, J. Med. Chem., 1988, 645 (c) A. J. Lin, M. Lee, and D. L. Klayman, J. Med. Chem. 1989, 32, 1249.
8. X. Luo, H. J. C. Yeh, A. Brossi, J. L. FlippenAnderson, and R. Gilardi, Helv. Chim. Acta, 67, 1515 (1984).
9. X. D. Luo and C. C. Shen, Medical Research Rev. 7, 29 (1987).
10. (a) I. S. Lee, H. N. ElSohly, E. M. Croom, and C. D. Hufford, J. Nat. Prod. 52, 337, 1989 (b) I. S. Lee, H. N. ElSohly and C. D. Hufford, Pharm. Res., 7, 199 (1990).
11. (a) R. A. Johnson, Oxidations in Organic Chemistry, Academic Press, Inc., pp. 131–210, 1978 (b) J. D. Fourneron, A. Archelas, B. Vigne and R. Furstoss, Tetrahedron, 43, 2273 (1987) and earlier references.
12. China Cooperative Research Group on Qinghaosu and Its Derivatives as Antimalarials, J. of Traditional Chinese Medicine, 2, 45 (1982).
13. M. M. Gottesman and I. Pastan, Trends in Pharmacological Science, 9, 54, (1988).
14. Y. Zhao, A. Li, P. Xie, H. Hou, W. Gu, M. Jia, X. Liu, and T. Lei, J. Med. Chem. 7, 287 (1987).
15. W. Xuan, Y. Zhao, A. Li, P. Xie, and Y. Cai, J. Med. Chem. 8, 282 (1988).

What is claimed is:

1. A method for hydroxylating a substrate selected from the group consisting of artemisinin, dihydroartemisinin, and a derivative of dihydroartemisinin, comprising incubating said substrate in the presence of *Beauveria sulfurescens* ATCC 7159 which introduces a hydroxyl group onto a methyl or methylene group therein, while preserving the peroxide bridge therein, thereby producing a hydroxylated derivative of said substrate, and recovering said hydroxylated derivative of said substrate.

2. The method of claim 1, wherein said substrate is selected from the group consisting of artemisinin, dihydroartemisinin, N-phenylcarbamoyl dihydroartemisinin, and arteether.

3. The method of claim 1, wherein said hydroxyl group is added at the C-7 or C-14 carbon of said substrate.

4. The method of claim 1, wherein said Beauveria sulfurescens ATCC 7159 is grown in a medium comprising dextrose and neopeptone.

5. The method of claim 1, wherein said incubating is carried out in phosphate buffer.

6. The method of claim 5, wherein the reaction product is extracted with an organic solvent.

7. The method of claim 6, wherein said organic solvent is ethyl acetate.

8. The method of claim 5, wherein mycelia obtained from 250 ml of media are resuspended in 100 ml of said phosphate buffer.

9. The method of claim 1, wherein said *Beauveria sulfurescens* ATCC 7159 is grown in a medium comprising corn steep liquors.

10. The method of claim 1, wherein said *Beauveria sulfurescens* ATCC 7159 is grown in Sabouraud liquid broth modified antibiotic medium 13.

11. The method of claim 10, wherein mycelia of said *Beauveria sulfurescens* ATCC 7159 are resuspended in 0.2 M phosphate buffer.

12. The method of claim 11, wherein said substrate is arteether.

13. The method of claim 1, wherein said hydroxylated derivative is selected from the group consisting of 14-hydroxy-N-phenylcarbamoyl dihydroartemisinin,

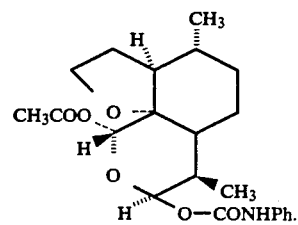

3α-hydroxyldesoxyarteether, 7β-hydroxyarteether, and 14-hydroxyarteether.

* * * * *